(12) United States Patent
Zhou et al.

(10) Patent No.: US 9,206,681 B2
(45) Date of Patent: Dec. 8, 2015

(54) WELLBORE FLUID TESTING ASSEMBLY

(71) Applicant: Superior Graphite Co., Chicago, IL (US)

(72) Inventors: Changjun Zhou, Chicago, IL (US); James L. Bruley, Oak Lawn, IL (US); Jess Maruri Garcia, New Lenox, IL (US)

(73) Assignee: Superior Graphite Co., Chicago, IL (US)

( * ) Notice: Subject to any disclaimer, the term of this patent is extended or adjusted under 35 U.S.C. 154(b) by 389 days.

(21) Appl. No.: 13/761,791

(22) Filed: Feb. 7, 2013

(65) Prior Publication Data

US 2014/0216149 A1   Aug. 7, 2014

(51) Int. Cl.
  *G01N 33/28*   (2006.01)
  *E21B 47/00*   (2012.01)
(52) U.S. Cl.
  CPC ............ *E21B 47/00* (2013.01); *G01N 33/2823* (2013.01)
(58) Field of Classification Search
  CPC ....................... G01N 33/2823; G01N 15/0806
  See application file for complete search history.

(56) References Cited

U.S. PATENT DOCUMENTS

| | | | | |
|---|---|---|---|---|
| 2,618,151 A | * | 11/1952 | Leas ................................... | 73/38 |
| 2,646,678 A | * | 7/1953 | Standing et al. .............. | 210/455 |
| 2,733,595 A | * | 2/1956 | Twining ............................. | 73/38 |
| 2,842,958 A | * | 7/1958 | Roark et al. ...................... | 73/38 |
| 3,172,286 A | * | 3/1965 | Cave et al. .................... | 73/61.64 |
| 3,289,467 A | * | 12/1966 | Parker et al. .................. | 73/61.63 |
| 3,324,712 A | * | 6/1967 | Watson et al. ................ | 73/61.63 |
| 3,574,099 A | * | 4/1971 | Ryans et al. .................... | 507/104 |
| 4,610,158 A | * | 9/1986 | Lawton, Jr. ................... | 73/61.64 |
| 4,748,849 A | * | 6/1988 | Jamison et al. .............. | 73/61.64 |
| 8,151,633 B2 | | 4/2012 | Jamison et al. | |
| 8,863,567 B2 | * | 10/2014 | Jappy et al. .................. | 73/61.64 |
| 2011/0290012 A1 | * | 12/2011 | Jappy et al. ................. | 73/152.55 |
| 2011/0295509 A1 | | 12/2011 | Huynh et al. | |

(Continued)

FOREIGN PATENT DOCUMENTS

WO   2008-112795   9/2008

OTHER PUBLICATIONS

OFI Testing Equipment, Inc., Permeability Plugging Tester—P.P.T., Instruction Manual, May 6, 2011, cover page and pp. 1-19, Version 2.2, OFI Testing Equipment, Inc., Houston,Texas.

(Continued)

*Primary Examiner* — John Fitzgerald
(74) *Attorney, Agent, or Firm* — Cook Alex Ltd.

(57) ABSTRACT

An assembly for the test chamber of a wellbore fluid testing apparatus for simulating fractures in a wellbore is provided comprising base plate of a first diameter having an aperture therethrough configured to be removably secured within the test chamber. A solid end plate of a second diameter smaller than the first diameter is provided that is removably secured to the base plate. One or more intermediate plates is provided that is located between the base plate and the end plate, each intermediate plate also having an aperture therethrough. At least one shim or spacer is provided to space the intermediate plates from any adjacent intermediate plate and/or to space the end plate from the adjacent intermediate plate. The spacer is configured to be removably secured to the assembly and to permit fluid flow in in the assembly through the aperture in the base plate and the opposed face of the intermediate plate and an adjacent intermediate plate or the base plate.

7 Claims, 3 Drawing Sheets

(56) References Cited

U.S. PATENT DOCUMENTS

2012/0316089 A1    12/2012  Kulkarni et al.
2013/0192358 A1*    8/2013  Murphy et al. ............ 73/152.05

OTHER PUBLICATIONS

Adel A. Al-Ansari, Faisal M. Al-Mutair, M.H. Al-Kilani, Saleh A. Al-Haidary, Mishal S. Al-Baloosh, A. A. Al-Nimer, Walid G. Al-Zahrani, Saudi Aramco, Vickneswaran Veloo, Mario Villalobos, Baker Hughes Drilling Fluids, SPE Members, Specially Formulated Drilling Fluid Prevents Differential Sticking, Mud Losses, and Wellbore Instability in Oil and Gas Wells in Saudi Arabia SPE 124087, paper, 2009, SPE/IADC Middle East Drilling Technology Conference & Exhibition held in Manama, Bahrain, Oct. 26-28, 2009.

* cited by examiner

WELLBORE FLUID TESTING ASSEMBLY

BACKGROUND

During drilling of a wellbore through subterranean rock formations, fluids are used for various purposes. The fluids cool and lubricate the drill string, carry drill cuttings to the surface, provide sufficient hydrostatic pressure to inhibit the ingress of formation fluids into the wellbore, etc. Drilling fluids may also contain additives, for example, fluid loss control agents to prevent the loss of drilling fluid into pores or fractures preexisting in the rock formation or induced by drilling action.

Apparatus for testing the efficacy of drilling fluid additives as fluid loss control agents are known. Such apparatus typically comprise a filter press including a pressure cell with a fluid inlet, a fluid outlet and a fluid-permeable medium secured within the pressure to simulate rock formation pores or fractures and so predict whether certain additives are capable of entering fractures in susceptible formations to plug the fracture. The fluid-permeable medium may be a ceramic filter disk that is secured in the outlet cap of the pressure cell. Typically, a plurality of filter disks is provided that vary in porosity so that differently-sized pores or fractures can be simulated. Such a testing device is available from, e.g., OFI Testing Equipment, Inc., of Houston, Tex., as the "Permeability Plugging Tester," (for which the Instruction Manual is attached to this disclosure as Appendix A). See also, e.g., US 2011/0295509, and WO 2008/112795, both of which are incorporated by reference herein. Machined disks with opening slots, such as those illustrated in SPE 124087, are often used to simulate fractures that are 200 microns or larger.

By way of the present disclosure, an assembly is provided for simulating fractures in a wellbore to be used in combination with the pressure cell of a filter press in place of the ceramic filter disks and machined disks described above. More particularly, a fracture simulation assembly is provided in which the constituent parts may be selected to simulate fractures of varying size.

SUMMARY

In accordance with one aspect of the present disclosure, an assembly for the test chamber of a wellbore fluid testing apparatus for simulating fractures in a wellbore is provided comprising a base plate of a first diameter having an aperture extending therethrough and which is configured to be removably secured within the test chamber of a plugging tester. A solid end plate of a second diameter smaller than the first diameter is removably secured to the base plate with one or more intermediate plates being located between the base plate and the end plate. Each intermediate plate has opposed first and second faces and an aperture therethrough. One or more shims or spacers is provided to space the end plate from the adjacent intermediate plate and/or to space adjacent intermediate plates. The spacers are configured to be removably secured to the assembly and to form a fluid flow path in in the assembly through the aperture in the base plate and between the spaced-apart opposed faces of the end plate and adjacent intermediate plates, as well as through the apertures of the intermediate plates.

In another aspect of the disclosure, the test assembly further comprises a plurality of intermediate plates, and the intermediates plates may have a thickness that varies in a radially outward direction.

In a further aspect, the base plate of the test assembly may have an intermediate plate formed integrally therewith and may include a second aperture therethrough in which a plug may be removably received. In such circumstances, the plug and aperture in the base plate may be formed with complementarily-shaped screw threads.

In another aspect of the disclosure, the assembly may comprise a plurality of fasteners removably securing together the base plate, end plate, one or more intermediate plates, and the one or more spacers.

In a further aspect of the disclosure, any of the thickness of the shims, the number of intermediate plates, and the degree of taper of the faces of the intermediate plates may be selected by the tester to simulate fractures of differing sizes In addition, a wellbore fluid testing apparatus is provided comprising a plugging tester having a pressure cylinder with an assembly for simulating fractures in a wellbore removably secured therein according to any of the aspects set forth above.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
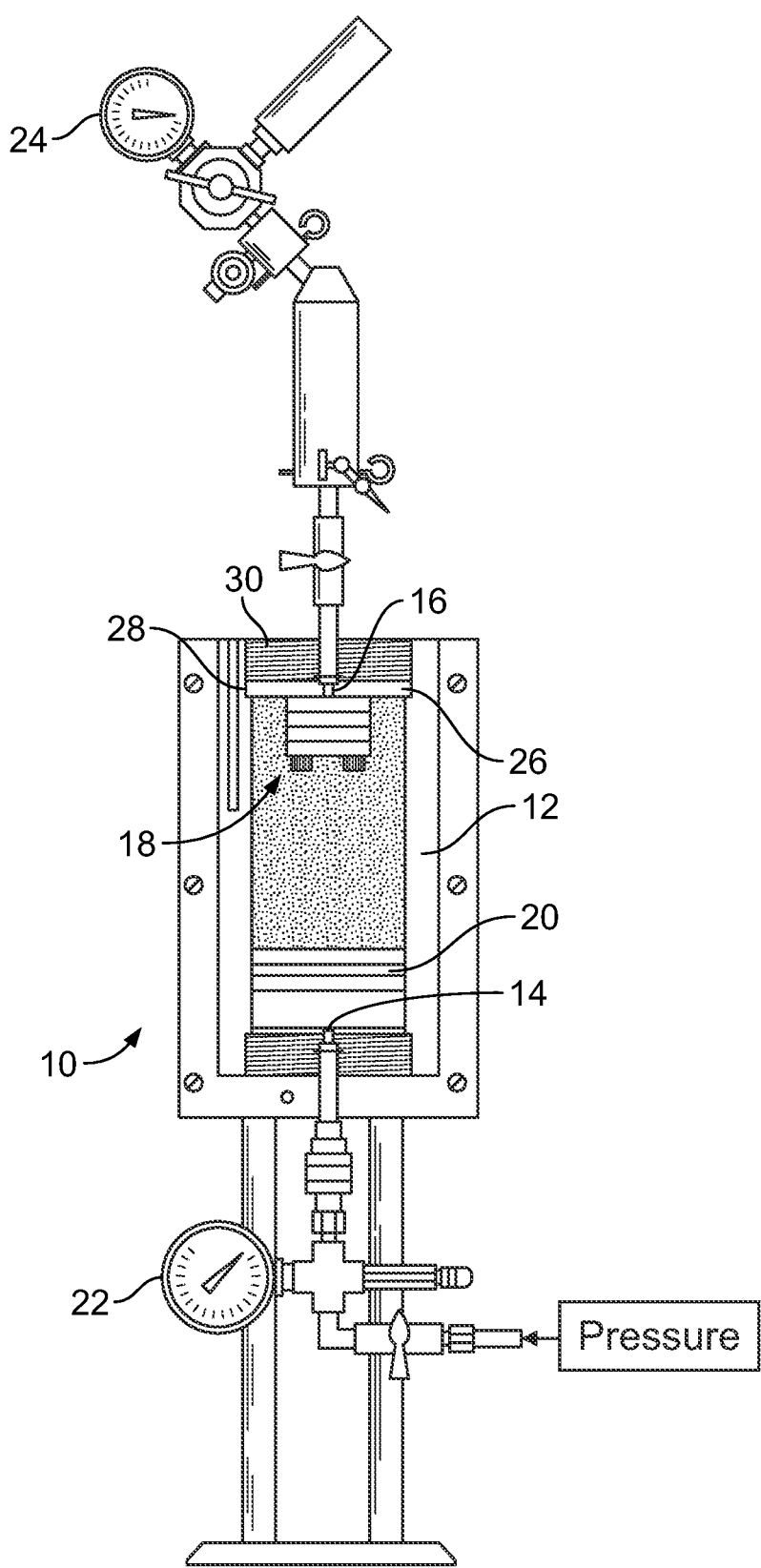
FIG. 1 is an elevational view of a permeability plugging tester, with the pressure cylinder shown in cross-section, having a fracture simulation assembly according to the present disclosure associated therewith.

Turning to FIG. 1, there is seen a permeability plugging tester ("PPT"), generally designated 10, that may be used for testing the efficacy of drilling fluid additives in plugging fractures in a wellbore through which drilling fluid might otherwise be lost. The PPT 10 is available from OH Testing Equipment, Inc. as part no. 171-84. The PPT 10 includes a test chamber or cylinder 12 with an inlet 14 and an outlet 16.

In accordance with the present disclosure a fracture simulation assembly ("FSA") 18 is removably secured within the test cylinder 12 adjacent the outlet 16. The FSA 18 has a flowpath therethrough intended to simulate a fracture in a wellbore. The drilling fluid to be tested is received within the test cylinder 12 between the FSA 18 and a slidable piston 20. When pressure is applied to the piston 20 through the inlet 14 by means of, e.g., a hydraulic pump (not shown), the drilling fluid will be placed under pressure to try to force it through the outlet 16 of the test cylinder 12. However, before passing through the outlet 16, the drilling fluid must pass through the FSA 18.

If the drilling fluid includes additives that successfully plug wellbore fractures, the flowpath through the FSA 18 will become blocked or clogged, thus preventing the drilling fluid from passing through the outlet 16 of the test cylinder. The PPT 10 includes pressure gauges 22 and 24, associated with the inlet 14 and the outlet 16, respectively, of the test cylinder 12. The volume of fluid collected during testing is used to assess the efficacy of the additive for plugging fractures under the testing condition.

As noted above, a PPT 10, such as that shown in FIG. 1, typically includes a plurality of porous ceramic disks or machined disks that are secured within the test cylinder to simulate wellbore fractures of various sizes dependent on the porosity of the ceramic disk or the size of the slots in the machined disk. In accordance with the present disclosure a FSA 18 is provided comprising a plurality of parts that may be selectively assembled together to simulate wellbore fractures of various sizes, thus eliminating the need for having a plurality of ceramic disks of different porosities or machined disks of different slot sizes.

Figure 2:
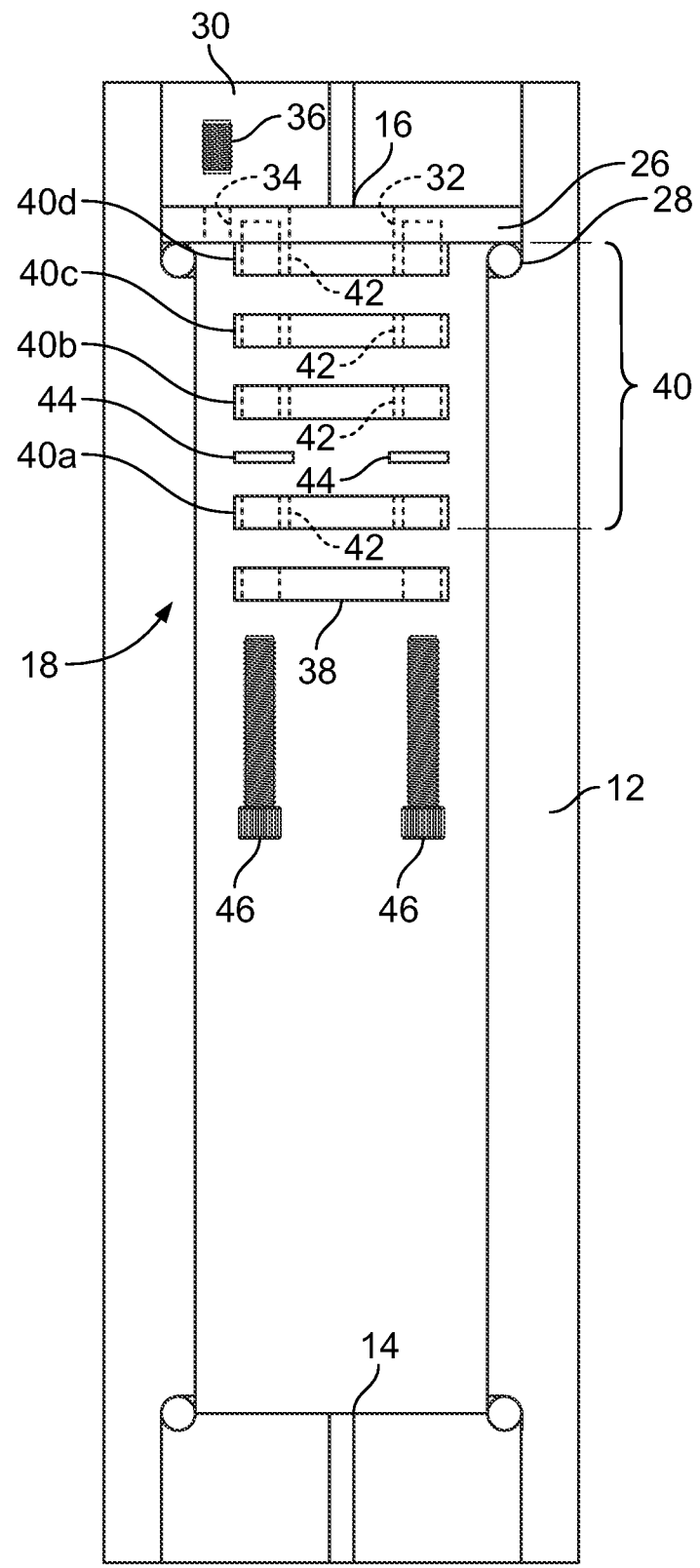
FIG. 2 is an enlarged elevational view of the pressure cylinder with the fracture simulation assembly in exploded condition shown in conjunction therewith.

Turning to FIG. 2, there is seen a FSA 18 in combination with the test cylinder 12 of the PPT 10. As illustrated, the FSA 18 includes a base plate 26 sized in diameter so as to seat on a shoulder 28 at the outlet end of the test cylinder 12 and to be secured within the test cylinder 12 by the end cap 30. When used in combination with the OFI PPT referred to above, the base plate has an outside diameter of approximately 2.50".

Figure 3:
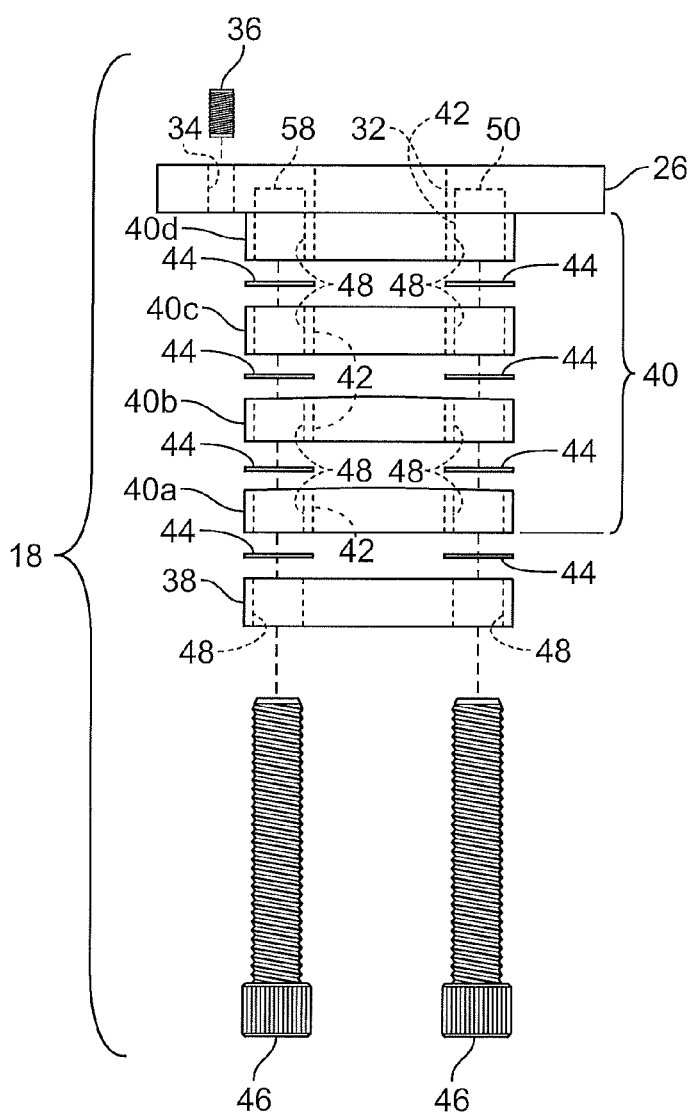
FIG. 3 is an exploded view of the fracture simulation assembly according to the present disclosure.

As best seen in FIG. 3, the base plate 26 comprises a generally flat disk and includes an orifice or aperture 32 preferably centrally located therein that forms part of the flowpath through the FSA 18 to provide a fluid path to the outlet 16. The base plate 26 also preferably includes a second aperture 34 therethrough that is closed by a removable plug 36 to allow for evacuation of trapped air within the test cylinder 12 prior to subjecting the drilling fluid within the test cylinder to test pressure. The aperture 34 and plug 36 may be formed with complementarily-shaped screw threads to facilitate opening and closing of the aperture 34.

The FSA 18 also includes an end plate 38 also comprising generally flat disk. The end plate 38 has a diameter smaller than that of the base plate 26 so that it fits within the test cylinder 12 with a space between the interior wall of the test cylinder and the outer edge of the end plate. When the FSA 18 is used in combination with the OFI PPT, the outside diameter of the end plate is approximately 1.50". In contrast to the base plate 26, the end plate 38 does not include an orifice or aperture that forms part of the flow path through the FSA 18.

Between the base plate 26 and the end plate 38 are one or more intermediate plates, collectively designated 40. As illustrated in FIG. 2, four intermediate plates 40a, 40b, 40c, and 40d, are shown. Each of the intermediate plates 40 includes a centrally-located orifice or aperture 42 therethrough, which forms part of the flowpath through the FSA 18. Optionally, the intermediate plate 40d may be formed integrally with the base plate 26. Otherwise, each of the intermediate plates 40 may be formed separately. As shown, the outside diameter of the intermediate plates 40 is the same as the outside diameter of the end plate 38.

In order to create a flowpath in the FSA 18 between the interior of the test cylinder 12 and through the orifices 42 in the intermediate plates 40 and the orifice 32 in the base plate 26 to the outlet 16, the FSA 18 includes at least one shim or spacer 44 between at least one of the intermediate plates 40 and an adjacent intermediate plate. As illustrated in FIG. 2, a spacer or shim 44 is placed between intermediate plates 40a and 40b. Thus, a flowpath is created in the FSA 18 from the interior of the test cylinder 12, between the opposed faces of plates 40a and 40b, through the orifices 42 in the intermediate plates 40 and the orifice 32 in the base plate 26, and out of the test cylinder 12 through the outlet 16. However, a spacer or shim 44 could be placed between each adjacent intermediate plate 40, between the end plate and the adjacent intermediate plate, and/or between the base plate and the adjacent intermediate plate. In FIG. 3, for example, spacers 44 are placed between each of the intermediate plates 40a, 40b, 40c, and 40d, and also between the intermediate plate 40a and end plate 38.

The thickness of the spacers 44 may be selected to simulate wellbore fractures of different sizes. By way of example, spacers 44 may be provided having thicknesses of 0.008" (203.2 microns), 0.012" (304.8 microns), 0.016" (406.4 microns), 0.020" (508 microns), 0.048" (1219 microns) and 0.060" (1524 microns), and the spacers may be used either singly, or in combination with other spacers. This range of sizing for the spacers and their combinations permits assembly of a FSA 18 for testing over a wide size range of fluid additives and simulated fracture sizes.

The base plate 26, intermediate plate(s) 40, end plate 38, and spacer(s) 44 are removably secured together in an assembly by means of one or more fasteners 46. As illustrated, the fasteners comprise a plurality of threaded bolts that are placed through complementarily-sized apertures 48 in the intermediate plate(s) 40, end plate 38, and spacers 44, and received in threaded blind apertures 50 in the base plate 26. As such, a spacer 44 corresponding to each fastener 46 is provided, with the spacers 44 being similar to washers that are received on the shafts of the fasteners.

Figure 4:
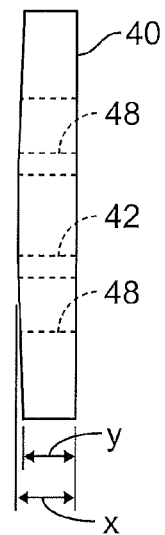
FIG. 4 is a side view of an intermediate plate for the fracture simulation assembly of the present disclosure having a single-tapered face.
Figure 5:
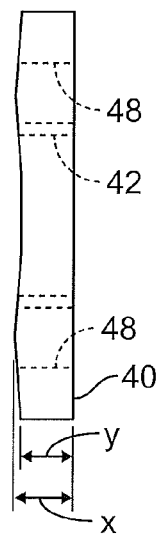
FIG. 5 is a side view of an intermediate plate for the fracture simulation assembly of the present disclosure having a double-tapered face.

In keeping with another aspect of the disclosure the faces of the intermediate plates 40 may be configured so as to provide various flow path configurations in the space created between the intermediate plates 40 by the spacers 44. For example, the intermediate plates 40 may be configured so that the thickness of the plate varies from the central orifice 42 to the outer edge. For, example, the intermediate plates 40 may be configured to have a single taper so that the thickness of the plate decreases from the center toward the outer edge. This creates a flow path between the intermediate plates 40 that decreases in size as the orifice 42 is approached. Alternatively, the intermediate plate may have a double taper, as shown in FIG. 5, where the thickness of the plate decreases both toward the center and toward the edge from a central peak. While FIGS. 4 and 5 show intermediate plates having one face tapered, both faces could be tapered, if desired.

In practice, the various plates 26, 38 and 40 of the FSA may be made of stainless steel and have an overall thickness X of approximately 0.25". Tapering a face of an intermediate plate 40 as shown in FIGS. 4 and 5 preferably results in the plate having a minimum thickness Y of approximately 0.24". Alternatively, the faces of the intermediate plates 38 may be formed with grooves, slots, or the like to create a more tortuous flow path through the FSA 18. The selection of material permits the FSA 18 to be safely heated during testing to better simulate actual downhole conditions.

When used with a plugging permeability tester, such as that designated 10 and shown in FIG. 1, the number of intermediate plates and spacers can be selected so that the FSA assembled therefrom can realistically approximate a great number of different fracture conditions that may be encountered. Also, a more realistic approximation of field conditions may be obtained during testing if the fluid pressure in the test cylinder is oscillated during the test, rather than being held substantially constant.

Thus, a fracture simulation assembly for use with a permeability plugging tester for drilling fluids has been disclosed. While the assembly has been described in terms of a preferred embodiment, there is no intent to limit it to the same, but to include modifications and variations as would be apparent to a person of ordinary skill in the art.

The invention claimed is:

1. A wellbore fluid testing apparatus comprising:
   a plugging tester including a pressure cylinder having a hollow interior defined by an interior wall and end walls of the cylinder and having a piston slidable therein;
   a fracture simulation assembly for simulating fractures in a wellbore removably secured within the pressure cylinder; the fracture simulation assembly further comprising:
   a base plate of a first diameter having an aperture therethrough configured to be removably secured within the test chamber;
   a solid end plate of a second diameter smaller than the first diameter removably secured to the base plate;
   one or more intermediate plates located between the base plate and the end plate, each intermediate plate having opposed first and second faces and an aperture therethrough, at least one of the intermediate plates having a thickness that varies in a radially outward direction and is uniform at any specific radial dimension;
   at least one spacer to space at least one intermediate plate from any adjacent intermediate plate and/or the end plate, the spacer configured to be removably secured to the fracture simulation assembly and to permit fluid flow in in the fracture simulation assembly through the aperture in the base plate and between spaced-apart base plate and intermediate plates; and
   a plurality of fasteners extending through each of the end plate, one or more intermediate plates, one or more spacers, and into the base plate to removably secure together the fracture simulation assembly within the cylinder of the wellbore fluid testing apparatus by means of one of the end caps so as to define a circumferential space between the fracture simulation assembly and the interior wall of the cylinder.

2. The wellbore fluid testing apparatus of claim 1 wherein the fracture simulation assembly further comprises a plurality of intermediate plates.

3. The wellbore fluid testing apparatus of claim 1 wherein the intermediate plates of the fracture simulation assembly have an edge thickness that is different from a central thickness.

4. The wellbore fluid testing apparatus of claim 1 wherein the intermediate plates of the fracture simulation assembly have an edge thickness that is less than a central thickness.

5. The wellbore fluid testing apparatus of claim 1 wherein the base plate of the fracture simulation assembly has an intermediate plate formed integrally therewith.

6. The wellbore fluid testing apparatus of claim 1 wherein the fracture simulation assembly further comprises a plurality of intermediate plates.

7. The wellbore fluid testing apparatus of claim 6 wherein the base plate of the fracture simulation assembly has an intermediate plate formed integrally therewith.

* * * * *